United States Patent [19]

Miyamoto et al.

[11] Patent Number: 4,954,530

[45] Date of Patent: Sep. 4, 1990

[54] PREVENTING AGENT FOR HUMAN IMMUNODEFICIENCY VIRUS INFECTION COMPRISING MENFEGOL

[75] Inventors: Tsutomu Miyamoto; Hisanaga Igarashi, both of Nagasaki; Sugiyama Hidenori, Tokyo, all of Japan

[73] Assignee: Eisai Co., Ltd., Tokyo, Japan

[21] Appl. No.: 356,367

[22] Filed: May 24, 1989

[30] Foreign Application Priority Data

May 25, 1988 [JP] Japan .................. 63-125661

[51] Int. Cl.$^5$ .................. A61K 31/075; A61K 31/74
[52] U.S. Cl. ...................... 514/718; 424/78
[58] Field of Search .................. 514/718; 424/78

[56] References Cited

PUBLICATIONS

Chemical Abstracts 94:109158z (1981).
Chemical Abstracts 99:82663z (1983).
Chemical Abstracts 101:185332e (1984).
Chemical Abstracts 103:774a (1985).

*Primary Examiner*—Jerome D. Goldberg
*Attorney, Agent, or Firm*—Wenderoth, Lind & Ponack

[57] ABSTRACT

Preventing agent for a human immunodeficiency virus infection contains menfegol as an active ingredient. The preventing agent may be in the form of a foaming tablet, a jelly preparation, vaginal suppository, or ointment. A condom applied with the jelly preparation is also disclosed.

4 Claims, No Drawings

PREVENTING AGENT FOR HUMAN IMMUNODEFICIENCY VIRUS INFECTION COMPRISING MENFEGOL

BACKGROUND OF THE INVENTION (1) Field of the Invention:

This invention relates to an agent for preventing human immunodeficiency virus (HIV) infection suitable for external application, which comprises menfegol as an active ingredient. More specifically, this invention is concerned with a preventing agent for HIV infection which contains menfegol as an active ingredient in a form of a gel preparation, foaming tablets, an ointment, vaginal suppositories or the like. This invention also embraces therein condoms, with said gel (2) Description of the Related Art:

Acquired immunodeficiency syndrome (AIDS) is a disease caused by cytopathogenicity and a decrease of helper T cells (Cluster of Differentiation type 4 antigen positive cells) due to infection by HIV. AIDS patients will go on to develop opportunistic infections such as pneumocytis carinii pneumonia and malignant tumors like Kaposi's sarcoma, etc., resulting in their deaths eventually. Although HIV infection may take place by breast-feeding, the administration of a blood preparation, etc., it occurs above all by heterosexual or homosexual intercourse. Thus, the increase of AIDS patients has become a serious social problem in recent years. A wide variety of research has been conducted for the prevention and treatment of AIDS, but no AIDS drug whose effectiveness has been confirmed has yet been developed. For the prevention of AIDS, it is hence important to avoid HIV infection. Use of condoms is recommended for this purpose, condoms are however accompanied by a potential danger of breakage or slip-off and are not considered to be perfect for the prevention of HIV infection.

SUMMARY OF THE INVENTION

An object of this invention is to provide a preventing agent for HIV infection suitable for external application.

Another object of this invention is to provide a condom with such an HIV infection preventing agent.

It has now been found that menfegol has strong anti-HIV activity, and is useful for preventing AIDS.

Menfegol, i.e. p-menthanylphenyl polyoxy-ethylene (8.8) ether having an average molecular weight of 620.03, is a nonionic surfactant. Menfegol has been used widely as a spermatocide, but other medical uses are yet unknown.

In one aspect of this invention, there is thus provided an agent for preventing HIV infection comprising menfegol as an active ingredient. The HIV infection preventive may preferably be in the form of a gel preparation, foaming tablets, ointment or vaginal suppositories.

In another aspect of this invention, there is also provided a condom with said gel preparation applied thereto.

According to this invention, menfegol can be formulated into a preparation form suitable for usual external application, for example, gel preparations, foaming tablets, ointment, vaginal suppositories, etc. Application of such a preparation into the vagina before coitus makes it possible to prevent HIV infection. In the case of a gel preparation, it can be used along with a condom to prevent HIV infection doubly.

DETAILED DESCRIPTION OF THE INVENTION AND PREFERRED EMBODIMENTS

Menfegol can be prepared, for example, by using turpentine oil as a starting material. Turpentine oil is converted into p-menthanylphenol via p-menthadiene and p-menthene. p-Menthanylphenol is then reacted with ethylene oxide in the presence of an alkali catalyst to obtain menfegol. [see K. Furuse: Perfumerie Cosmetique Savons, 10, 342 (1967)].

Although menfegol is considered to be effective when used in an amount of 2 mg per dose in view of its anti-HIV activities and the sperm volume (normally, about 10 ml) per ejaculation, it is preferable to use it in an amount of 10-100 mg per each dose to ensure its sufficient effect.

Anti-HIV effects of menfegol and menfegol-containing preparations according to this invention will be demonstrated in the following examples.

EXAMPLE 1

Anti-HIV Test

In this test, there was used, as an HIV strain, lymphadenopathy associated virus (LAV) which was allowed to grow in CEM cells, a cell strain of the CD4+T cell line (Cluster of Differentiation type 4 antigen positive cell line). The LAV was furnished by Pasteur Institute, France.

The following cells and virus culture operations were all carried out at 37° C. in a $CO_2$ incubator.

CEM cells ($1 \times 10^7$ cells/ml) infected with LAV (antigen expression rate: 80–100%) were cultured overnight in RPMI-1640 medium containing 10 mM of N-2-hydroxyethyl-piperazine-N-2-ethanesulfonic acid and 10% of fetal calf serum (hereinafter called the "medium A"). The virus preparation in culture medium was divided into 6 portions. Five portions were added with menfegol to give final concentrations of 2.5 mM, 1.0 mM, 0.25 mM, 0.0625 mM and 0.0156 mM, respectively. The remaining portion was added with the same volume of the medium A to provide a control. After incubating those mixtures of virus and menfegol at room temperature for 5 minutes to allow menfegol act on the LAV, those were applied on Sephadex G-200 (trade name Product of Pharmacia AB) which was swollen by distilled water and equilibrated with medium A. By the spin column technique (2,000 rpm, 30 seconds), menfegol was removed from the respective mixtures. Removal of menfegol was carried out for eliminating any direct cytotoxicity of menfegol against T-lymphocytes.

On the other hand, 100 μl of MT-4 cells (a T lymphocyte strain of the Cluster of Differentiation type 4 antigen positive cell line) suspended at $5 \times 10^5$ cells/ml in the medium A were added to the respective wells of a plastic plate (8 rows×12 columns) for tissue culture. Then, the wells were added respectively 100 μl portions of tenfold stepwise ($10^0$–$10^{-9}$) diluted solutions of the menfegol-removed virus sample. After 10-days incubation, the virus titer ($TCID_{50}$) in each sample was determined by the triple blank test, using the indirect fluorescent antibody technique.

The results are shown in the following table.

| Amount of menfegol added, mM | Virus Titer, (TCID$_{50}$/ml) |
|---|---|
| 0 (Control) | $10^{5.13}$ |
| 2.5 | $<10^{0.3}$ |
| 1.0 | $<10^{0.3}$ |
| 0.25 | $<10^{0.3}$ |
| 0.0625 | $<10^{3.13}$ |
| 0.0156 | $<10^{4.47}$ |

From the foregoing results, menfegol has been found to completely inactivate the HIV at a concentration of at least 0.25 mM (0.016% w/v).

EXAMPLE 2

| Foaming Tablets | |
|---|---|
| Ingredient | Weight per tablet, mg |
| Menfegol | 60.0 |
| Dioctyl sodium sulfosuccinate | 5.0 |
| Dried egg albumen | 12.5 |
| Light silicic anhydride | 105.0 |
| Crystalline cellulose | 30.0 |
| Potassium hydrogentartrate | 326.0 |
| Sodium bicarbonate | 160.0 |
| Polyvinylpyrrolidone (K-30) | 17.0 |
| Corn starch | 84.5 |
| TOTAL | 800.0 |

Preparation

Light silicic anhydride (⅔ portion), potassium hydrogentartrate and corn starch were mixed, to which menfegol, a solution of dioctyl sodium sulfosuccinate in a mixture of water and ethanol (1:1 V/V) and an aqueous solution of polyvinylpyrrolidone (K-30) were added successively. The resulting mixture was mixed thoroughly, granulated, and then dried to obtain menfegol-containing granules.

Light silicic anhydride (⅓ portion), sodium bicarbonate and crystalline cellulose were mixed thoroughly, to which the menfegol-containing granules prepared above were added, followed by the addition of dried egg albumen. The resulting mixture was mixed uniformly. The thus-obtained mixture was compressed into tablets having a weight of 800 mg. The thus-obtained tablets contain 60.0 mg of menfegol.

EXAMPLE 3:

Gel Preparation

| Ingredient | Weight, mg |
|---|---|
| Menfegol | 20.00 |
| Polyethylene glycol #400 | 519.40 |
| Polyethylene glycol #4000 | 60.00 |
| Methylparaben | 0.45 |
| Propylparaben | 0.15 |
| TOTAL | 600.00 |

Preparation

Polyethylene glycol #400 and polyethylene glycol #4000 were melted at 60°-65° C. To the melt, menfegol, methylparaben and propylparaben were added successively under stirring, at the same temperature. The resulting mixture was stirred intimately and then allowed to cool gradually to room temperature, thereby obtaining a gel preparation.

EXAMPLE 4:

Condom with gel preparation

A gel preparation (600 mg), which had been formulated in accordance with Example 3, was heated to about 80° C. to enhance its flowability. In this state, the gel preparation was added dropwise to an inner tip wall portion (semen catch) of a main body of a condom and was then allowed to cool to room temperature gradually. A condom applied with the gel preparation applied was thus obtained.

What is claimed is:

1. A method for the prevention of human immunodeficiency virus infection which comprises causing male semen of an infected male at the time of ejaculation to come into contact with a preparation which comprises menfegol as an active ingredient in an amount ranging from 10 to 100 mg per dose and a pharmaceutically acceptable carrier therefor.

2. A method according to claim 1 wherein the preparation is in the form of a foaming tablet.

3. A method according to claim 1 wherein the preparation is in the form of a gel.

4. A method according to claim 1 wherein the preparation is in a gel form and is contained in a condom.

* * * * *